US011202589B2

United States Patent
Albuquerque et al.

(10) Patent No.: US 11,202,589 B2
(45) Date of Patent: Dec. 21, 2021

(54) SYSTEM AND METHOD FOR ASSESSMENT OF RETINAL AND CHOROIDAL BLOOD FLOW NONINVASIVELY USING COLOR AMPLIFICATION

(71) Applicant: University of Kentucky Research Foundation, Lexington, KY (US)

(72) Inventors: Romulo Albuquerque, Lexington, KY (US); Nicholas Bell, Lexington, KY (US); Paras Vora, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 223 days.

(21) Appl. No.: 16/206,039

(22) Filed: Nov. 30, 2018

(65) Prior Publication Data

US 2019/0159707 A1  May 30, 2019

Related U.S. Application Data

(60) Provisional application No. 62/593,045, filed on Nov. 30, 2017.

(51) Int. Cl.
*A61B 5/02* (2006.01)
*A61B 5/1455* (2006.01)
(Continued)

(52) U.S. Cl.
CPC ........ *A61B 5/14555* (2013.01); *A61B 3/0041* (2013.01); *A61B 3/0083* (2013.01);
(Continued)

(58) Field of Classification Search
CPC ............ A61B 5/14555; A61B 5/02416; A61B 3/0041; A61B 3/0083; A61B 5/318; G06T 5/009; G06T 5/50
See application file for complete search history.

(56) References Cited

U.S. PATENT DOCUMENTS

2008/0317308 A1  12/2008  Wu et al.
2009/0226057 A1   9/2009  Mashiach et al.
(Continued)

OTHER PUBLICATIONS

Rezaeian, et al., High Speed in-Vivo Imaging of Retinal Hemodynamics in a Rodent Model of Hypertension, Published in 2016 38th Annual International Conference of the IEEE Engineering in Medicine and Biology Society (EMBC), pp. 3243-3246, Aug. 16, 2016.

(Continued)

*Primary Examiner* — Joel F Brutus
(74) *Attorney, Agent, or Firm* — Stites & Harbison PLLC; Jeffrey A. Haeberlin (57) ABSTRACT

A system and method for assessing blood flow include: an ocular lens; a light source; a digital video camera; a biosensor; a trigger; and a computer. The ocular lens is for viewing a fundus of an eye. The light source is for illuminating the fundus. The digital video camera is for imaging the fundus. The biosensor is for sensing a pulse waveform. The computer is configured for: recording input frames and pulse waveform data in response to an input from the trigger; defining a low-pass frequency and a high-pass frequency from the pulse waveform data; stabilizing the input frames; enhancing contrast of the input frames; separating the input frames into sub-channels; conducting eulerian video magnification for color amplification using the inputs of image sampling rate, the low-pass frequency, the high-pass frequency, and an amplification factor; reconstructing the sub-channels into output frames; and combining the output frames with the input frames.

16 Claims, 7 Drawing Sheets

(51) Int. Cl.
| | |
|---|---|
| *G06T 5/00* | (2006.01) |
| *G06T 5/50* | (2006.01) |
| *A61B 3/12* | (2006.01) |
| *A61B 3/00* | (2006.01) |
| *A61B 3/14* | (2006.01) |
| *G06T 5/40* | (2006.01) |
| *A61B 5/00* | (2006.01) |
| *A61B 5/024* | (2006.01) |
| *A61B 5/318* | (2021.01) |

(52) U.S. Cl.
CPC .......... *A61B 3/1233* (2013.01); *A61B 3/1241* (2013.01); *A61B 3/145* (2013.01); *G06T 5/009* (2013.01); *G06T 5/40* (2013.01); *G06T 5/50* (2013.01); *A61B 5/02416* (2013.01); *A61B 5/318* (2021.01); *A61B 5/6821* (2013.01); *A61B 5/7257* (2013.01); *G06T 2207/10016* (2013.01); *G06T 2207/20021* (2013.01); *G06T 2207/20056* (2013.01); *G06T 2207/20104* (2013.01); *G06T 2207/20212* (2013.01); *G06T 2207/30041* (2013.01); *G06T 2207/30104* (2013.01)

(56) References Cited

U.S. PATENT DOCUMENTS

| | | |
|---|---|---|
| 2013/0211285 A1 | 8/2013 | Fuller et al. |
| 2016/0262625 A1 | 9/2016 | Lawrenson et al. |
| 2017/0156608 A1 | 6/2017 | Mahar |

OTHER PUBLICATIONS

Kohli et al., Exact detection of optic disk in retinal images using segmentation based on level set method and morphological operations, Thesis, Thapar University, Patiala-147004, Jul. 2012. (PDF file is locked and cannot be uploaded, please see: https://www.google.com/url?sa=t&rct=j&q=&esrc=s&source=web&cd=1&ved=2ahUKEwjlsl-AvaPiAhVxmK0KHXsnCpMQFjAAegQIARAC&url=https%3A%2F%2Fpdfs.semanticscholar.org%2Fda35%2F5107e983671dd01b53ee7137010b1a11d000.pdf&usg=AOvVaw1pM-vtGSoHIZ_a4NoIB_qN).

Zhao et al., Applying Video Magnification Techniques to the visualization of blood flow, Thesis, Massachusetts Institute of Technology, Jun. 2015.

Brieva et al, Motion Magnification using the Hermite Transform, Proc. SPIE 9681, 11th International Symposium on Medical Information Processing and Analysis, 96810Q, Dec. 22, 2015.

Galbally et al., A Review of Iris Anti-Spoofing, 2016 4th International Conference on Biometrics and Forensics (IWBF), Mar. 3, 2016.

Zhu et al., Feasibility of Extracting Velocity Distribution in Choriocapillaris in Human Eyes from ICG Dye Angiograms, Journal of Biomechanical Engineering, Apr. 2006, pp. 203-209.

Zheng, A general model for multiphase texture segmentation and its applications to retinal image analysis, Biomedical Signal Processing and Control 8 (2013), 374-381.

SYSTEM AND METHOD FOR ASSESSMENT OF RETINAL AND CHOROIDAL BLOOD FLOW NONINVASIVELY USING COLOR AMPLIFICATION

RELATED APPLICATIONS

This application claims priority to U.S. Provisional Patent Application No. 62/593,045, filed Nov. 30, 2017, the entire disclosure of which is incorporated herein by reference.

STATEMENT REGARDING FEDERALLY SPONSORED RESEARCH OR DEVELOPMENT

The presently disclosed subject matter was made with support from the U.S. Government under Grant Number TL1TR001997 awarded by the National Institutes of Health. Thus, the U.S. Government has certain rights in the presently disclosed subject matter.

BACKGROUND OF THE INVENTION

1. Field of the Invention

The presently-disclosed subject matter relates to a system and method for assessment of retinal and choroidal blood flow noninvasively using color amplification.

2. Description of Related Art

Diabetic Retinopathy (DR) is an increasingly prevalent disease and a leading contributor of all-cause blindness worldwide. Approximately one-third of the nearly 285 million diabetes mellitus patients worldwide have signs of DR. In addition to retinal changes, choroidal abnormalities are common in patients with diabetes. The choroid—the vascular layer of the eye between the retina and the sclera—supplies blood to the outer layers of the retina including the retinal pigmented epithelium (RPE) and photoreceptors. Despite growing evidence of choroidal abnormalities present in diabetes, it remains unclear how these changes clinically impact diabetic patients. Decreased choroidal blood flow is thought to be the primary event leading to diabetic retinopathy. Therefore, it is critical to understand vascular development of and events leading to abnormalities of choroid vessels. Although the retina itself is readily available for imaging, the RPE obscures the choroid, making it difficult to visualize using standard ophthalmic imaging techniques. This difficulty hinders efforts in using choroidal abnormalities as a predictive factor of disease evolution and response. Indocyanine green (ICG) angiography, which utilizes a dye that can be seen through the RPE layer, has been used clinically to visualize choroidal vessel filling abnormalities in the eyes of patients with retinopathy. Although this technique can detect gross vascular defects, it does not provide much information concerning anatomic or structural features of the choroid, and it requires static images taken sequentially over minutes. Additionally, the ICG contrast dye is known to cause allergic reactions and requires venipuncture making the technique invasive to the patient. The National Eye Institute has identified the need to engineer and apply new methods and image processing techniques to study blood flow in the retina and choroid, with the ultimate goal of translating these imaging technologies into cost-effective and easy-to-use platforms for routine clinical use.

BRIEF SUMMARY OF THE INVENTION

In accordance with one aspect of the invention, a system for assessing retinal and choroidal blood flow in a subject, includes: an ocular lens; a light source; a digital video camera; a biosensor; a trigger; a computer; and a display. The ocular lens is for viewing a fundus of an eye of the subject. The light source is for illuminating the fundus of the eye of the subject. The digital video camera is in optical communication with the ocular lens for imaging the fundus of the eye of the subject. The biosensor is for sensing a pulse waveform of the subject. The computer is in communication with the digital video camera, the biosensor, and the trigger. The computer is configured for: recording input frames received from the digital video camera and pulse waveform data from the biosensor in response to an input from the trigger; defining a low-pass frequency and a high-pass frequency by a lowest time and a highest time between heart beats in the pulse waveform data; stabilizing each of the input frames utilizing subpixel phase correlation with a reference frame; enhancing contrast of each of the input frames utilizing contrast limited adaptive histogram equalization (CLAHE); separating each of the input frames into sub-channels; conducting on each sub-channel eulerian video magnification for color amplification using the inputs of image sampling rate, the low-pass frequency, the high-pass frequency, and an amplification factor; reconstructing the amplified sub-channels into output frames; and combining the output frames with the input frames, resulting in enhanced frames demonstrating retinal and choroidal blood flow and tissue perfusion. The display is for displaying the enhanced frames.

In one implementation, the system further includes a head and chin rest for the subject to rest comfortably without strain.

In another implementation, the system includes a fixation illuminator attached to the ocular lens to reduce ocular movements.

In yet another implementation, the biosensor is a pulse oximeter.

In another embodiment, the computer is further configured for adjusting the enhanced frames for brightness, contrast, zoom, or rotation.

In yet another embodiment, the computer is further configured for quantifying image intensity for a user-selected region of interest (ROI) and generating a heat map of the ROI where intensity changes are greatest.

The amplification factor may be a scalar, or may be function-based.

In accordance with another aspect of the invention, a method for assessing retinal and choroidal blood flow in a subject, includes: recording, by a computer in response to an input from a trigger, input frames received from a digital video camera and an ocular lens configured for imaging a fundus of an eye of the subject; recording, by the computer in response to the input from the trigger, pulse waveform data of the subject received from a biosensor; defining a low-pass frequency and a high-pass frequency by a lowest time and a highest time between heart beats in the pulse waveform data; stabilizing each of the input frames utilizing subpixel phase correlation with a reference frame; enhancing contrast of each of the input frames utilizing contrast limited adaptive histogram equalization (CLAHE); separating each of the input frames into sub-channels; conducting, on each sub-channel, eulerian video magnification for color amplification using the inputs of image sampling rate, the low-pass frequency, the high-pass frequency, and an amplification factor; reconstructing the amplified sub-channels into output frames; and combining the output frames with the input frames, resulting in enhanced frames demonstrating tissue perfusion.

In one implementation, the method further includes illuminating the eye of the subject with a fixation illuminator to reduce ocular movements.

In another implementation, the method further includes saving the enhanced frames sequentially to a video file. Alternatively, the method may further include displaying the enhanced frames live on a display.

In yet another implementation, the method further includes waiting to until enough pulse waveform data has been recorded to define the low-pass frequency and the high-pass frequency before stabilizing each and enhancing the contrast of each of the input frames.

In one embodiment, the pulse waveform data is a pulse oximeter signal, and the method further includes cross-correlating the pulse oximeter signal with the input frames, including: performing temporal fast fourier transform of the input frames; performing temporal fast fourier transform of the pulse oximeter signal; determining a matrix product by matrix multiplication of the temporal fast fourier transform of the image frames with a complex conjugate of the temporal fast fourier transform of the pulse oximeter signal; performing inverse fast fourier transform of the matrix product; determining a peak of the inverse fast fourier transform of the matrix product to obtain a time delay between the pulse oximeter signal land the image frames; and shifting the pulse oximeter signal by the time delay.

The amplification factor may be a scalar, or may be function-based.

DETAIL DESCRIPTION OF EXEMPLARY EMBODIMENTS

The details of one or more embodiments of the presently-disclosed invention are set forth in this document. Modifications to embodiments described herein, and other embodiments, will be evident to those of ordinary skill in the art after a study of the information provided herein. The information provided herein, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims.

The terms "computer," "computing machine," "processing device," and "processor" are used herein to describe one or more microprocessors, microcontrollers, central processing units, Digital Signal Processors (DSPs), Field-Programmable Gate Arrays (FPGAs), Application-Specific Integrated Circuits (ASICs), or the like, along with peripheral devices such as data storage device(s), input/output devices, or the like, for executing software instructions to perform substantial computations including numerous arithmetic operations or logic operations without human intervention during a run.

The term "data storage device" is understood to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks, and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

Eulerian Video Magnification (EVM), a technique developed at the Massachusetts Institute of Technology, amplifies small changes from seemingly static video, revealing subtle variations that would be otherwise invisible to the naked eye. This invention modifies and enhances EVM to further advance this technique specifically for retinal imaging. To do this, the invention involves the addition of pre-processing image stabilization to the EVM algorithm using reference points specific to the retina, as well as interfacing with other biosensors to continuously refine variables in the algorithm to improve sensitivity and quality. Advantageously, this invention provides an elegant, noninvasive, and inexpensive solution to assess retinal and choroidal blood flow.

As used herein, the term "perfusion" means the passage of fluid through the circulatory system or lymphatic system to an organ or a tissue, referring to the delivery of blood to a capillary bed in tissue. Perfusion is measured as the rate at which blood is delivered to tissue, or volume of blood per unit time (blood flow) per unit tissue mass.

Figure 1:
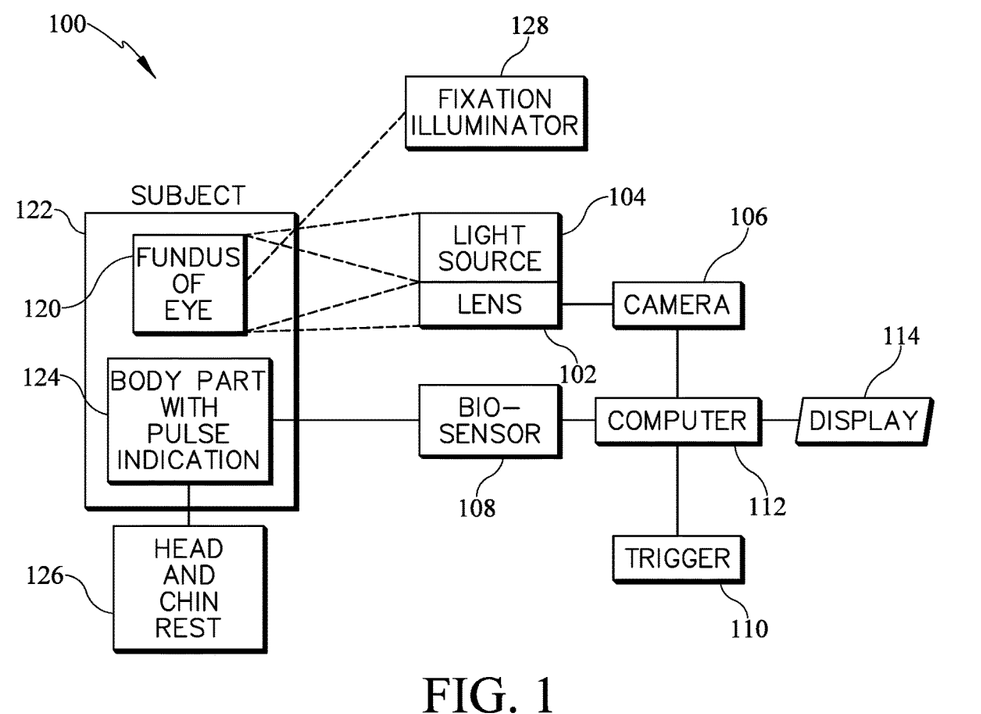
FIG. 1 is a schematic diagram of an exemplary system for assessing retinal and choroidal blood flow in a subject, according to the invention.

As shown in FIG. 1, an exemplary system 100 according to the invention includes an ocular lens 102, a light source 104, a digital video camera 106, a biosensor 108, a trigger 110, a computer 112, and a display 114.

Figure 2:
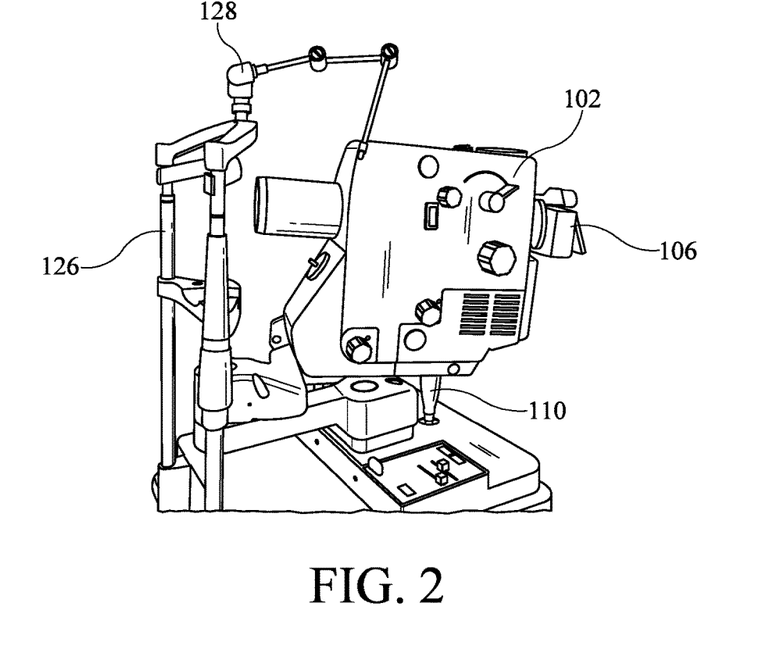
FIG. 2 is a perspective view of an exemplary apparatus including an ocular lens, digital video camera, and a head and chin rest, according to the invention.

The ocular lens 102 is configured for viewing a fundus of an eye 120 of a subject 122. The subject 122 is preferably a human being, but the exemplary system would also function on eyes of other living animals having a measurable pulse. In the exemplary embodiment, the ocular lens 102 is a fundus lens, such as a Topcon TRC-50X by Topcon Medical Systems, Oxland, N.J. (see: FIG. 2). Lenses providing different views of the fundus of the eye 120 (e.g., 20, 35, and 50 degree views) can be utilized. Further lenses can be used to give a zoomed view, or a more peripheral view. Additionally, adaptive optics can be used to account for distortions in focus caused by eye movements.

The light source 104 is for illuminating the fundus of the eye 120 of the subject 122. The light source 104 is preferably a coherent light source producing coherent illumination. However, the light source 104 may also be a laser, an incoherent light source, a light source producing differing intensities of light, or a light source producing different wavelengths of light. For example, a near-infrared (NIR) light source producing NIR wavelengths of light cause an autofluorescence of the retinal pigment epithelium (RPE), which allows visualized thinning of the RPE layer based on increased visualization of vasculature and blood flow, as discussed below. Furthermore, the light source 104 may strobe or pulse the illumination to reduce eye strain or to enable the use of higher intensity illumination.

The digital video camera 106 is interfaced to the ocular lens 102 (i.e., is in optical communication with the lens) (see: FIG. 2) for imaging the fundus of the eye 120 of the subject 122. The digital video camera 106 is preferably a consumer-grade digital video camera with a CMOS sensor, such as a Sony A7SII, by Sony Corporation of Tokyo, Japan. However, the digital video camera 106 may also be a more specialized camera having improved spatial resolution (over that of a consumer-grade camera), or may include other sensor types, such as CCD, or other wavelength sensitivities, such as NIR, green, blue, etc., or operate at higher temporal frequencies (e.g., 200, 500, 960 frames per second) to capture perfusion and blood flow in subjects having a higher heart rate/pulse.

The biosensor 108 is for sensing a pulse waveform of a body part having a pulse indication 124 of the subject 122. For instance, the biosensor 108 in one embodiment is a pulse oximeter that records oxygen saturation in a subject's finger via photoplethysmography providing a proxy for pulse. In another embodiment, the biosensor 108 is an electrocardiogram (EKG). In yet other embodiments, the biosensor 108 is a wearable device for photoplethysmography, a doppler ultrasound device, an echocardiogram device, and even, in an operating room environment, a catheter sensing a pulse/pressure waveform in a central line.

The trigger 110 in one embodiment is a hardware trigger including a joystick with a top button (see: FIG. 2). In other embodiments, the trigger is a software trigger, or an input from a keyboard, a capacitive or a resistive touch sensitive button, a touch screen, a game console controller, or a voice activated device.

The computer 112 in in communication with the digital video camera 106, the biosensor 108, and the trigger 110. In some embodiments, the computer 112 is a general purpose computer with a processor and a data storage device/memory. In other embodiments, the computer 112 is a FPGA dedicated to performing the functions discussed below. The computer 112 is configured for recording input frames received from the digital video camera 106 and pulse waveform data from the biosensor 108 in response to an input from the trigger 110. The computer 112 receives the input frames and the pulse waveform data simultaneously, once recording is initiated with the trigger 110. On each sample by the digital video camera 106, the biosensor 108 also senses the pulse waveform of the subject, providing a proxy for the pulse of the subject 122. The computer 112 syncs the input frames and the pulse waveform data based on the trigger 110 to record both the input frames and the pulse waveform.

The computer 112 is also configured for defining a low-pass frequency and a high-pass frequency by a lowest time and a highest time between heart beats in the pulse waveform data, stabilizing each of the input frames utilizing subpixel phase correlation with a reference frame, and enhancing contrast of each of the input frames utilizing contrast limited adaptive histogram equalization (CLAHE). Once a number of input frames have been recorded to obtain pulse variability (low pass and high pass frequency), the computer 112 begins stabilizing each of the input frames on a frame by frame basis utilizing subpixel registration based on phase correlation of the start frame. Then, the input frames undergo contrast enhancement the CLAHE method, in real time before obtaining the next frame. Advantageously, the integration of the biosensor allows narrowing of the frequency range of interest and boosting the signal-to-noise ratio of the resulting enhanced frames described below.

The computer 112 is further configured for separating each of the input frames into sub-channels (e.g., red, green, blue), and conducting on each sub-channel eulerian video magnification (EVM) for color amplification using the inputs of image sampling rate, the low-pass frequency, the high-pass frequency, and an amplification factor. In one embodiment, the amplification factor is a scalar. In another embodiment, the amplification factor is function-based. For example, in one embodiment, the pulse waveform sensed by the biosensor 108 is normalized and the normalized waveform is used as an amplification factor function, such that the amplification factor is maximized when the subject's blood flow/pressure is at a maximum and minimized when the subject's blood flow/pressure is at a minimum in the pulse waveform. Advantageously, the amplification factor makes perfusion visual without introducing signal artifacts.

Then, the computer 112 is for reconstructing the amplified sub-channels into output frames; and combining the output frames with the input frames, resulting in enhanced frames demonstrating retinal and choroidal blood flow and tissue perfusion. Then, the enhanced frames are either saved sequentially to a video file or viewed live on the display 114.

Thus, the invention continuously modifies the input variables to conducting Eulerian Video Magnification with feedback from the user and the outputs, along with pre-processing and post-processing in order to improve the quality of the output. In addition, the biosensor 108 provides another input variable.

The display 114 is for displaying the enhanced frames. In one embodiment, the display 114 is a general purpose computer display. In other embodiments, the display 114 is a virtual reality (VR) head-mounted display, an organic light-emitting diode (OLED) display, or a liquid crystal display (LCD). The computer 112 is further configured for adjusting the enhanced frames for brightness, contrast, zoom, rotation, and time, and outputting the enhanced frames to the display 114 to visualize retinal and choroidal blood flow and tissue perfusion.

The integration of the ocular lens 102, light source 104, and digital video camera 106 with the biosensor 108 and eulerian video magnification (EVM) is new from the prior art of other retina camera systems and of prior work accomplished with EVM. Signal cross-correlation of the input frames (i.e., image sampling) with the pulse waveform data (i.e., biosensor data) allows for timing the start and end of each pulse, which is used in conducting EVM. This system allows for visualization of microvasculature dynamics, which has not been done with other prior art that has utilized EVM.

The prior art, such as other applications of eulerian video magnification, standard retinal fundoscopy, and static images obtained through indocyanine green angiography, do not include the ability to visualize blood flow in areas specific to the retina. The tissue analyzed in prior art was performed on easily accessible tissue with large volumes of blood flow i.e. the hand. By integrating the ocular lens 102, the light source 104, the digital video camera 106, the biosensor 108, and the computer 112 (i.e., processing system), the exemplary system 100 is capable of blood flow visualization at a smaller scale with greater accuracy, allowing for a true readout specific to each individual in a minimally accessible tissue layer. Note that this is noninvasive, in that it does not utilize an intravenous contrast dye. The prior art also utilizes a rough estimate of heart rate to select a static low-pass and high-pass frequency for the eulerian video magnification step, which leads to artifacts and decreases signal to noise ratio. The exemplary system 100 records the heart rate with the biosensor 108 to more accurately enhance changes that correspond with tissue perfusion.

Additionally, the exemplary system 100 also includes a head and chin rest 126 for the subject to rest comfortably without strain. FIG. 2 shows an exemplary apparatus including an ocular lens 102, a digital video camera 106, and a head and chin rest 126.

Returning now to FIG. 1, the exemplary system 100 also includes a fixation illuminator 128. The fixation illuminator 128 is to reduce ocular movements.

In one embodiment, the computer 112 is further configured for quantifying image intensity for a user-selected region of interest (ROI) and generating a heat map of the ROI where intensity changes are greatest.

Figure 3:
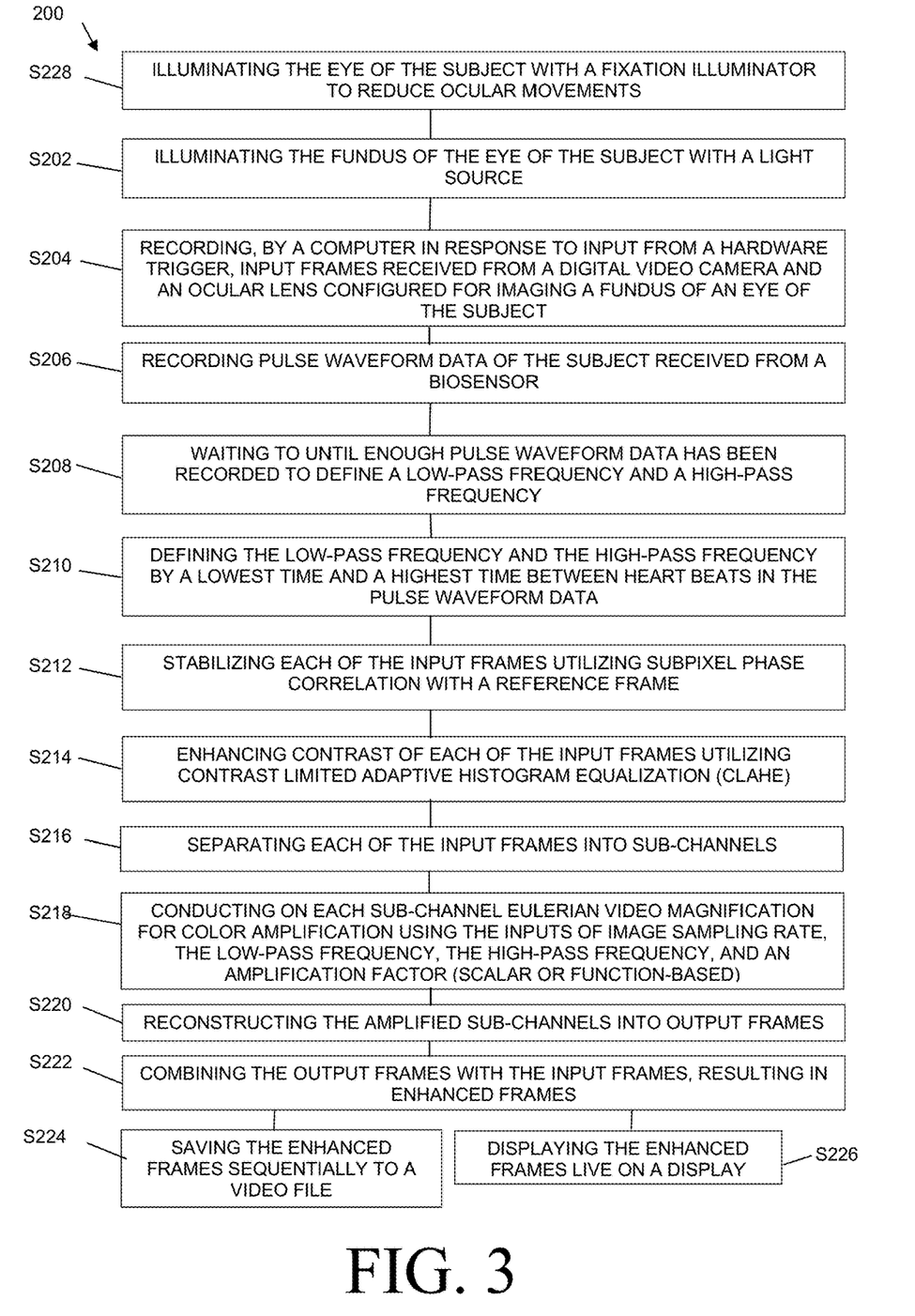
FIG. 3 is flow chart of an exemplary method for assessing retinal and choroidal blood flow in a subject, according to the invention.

FIG. 3 is a flow chart of an exemplary method 200 for assessing retinal and choroidal blood flow in a subject. The exemplary method 200 includes the steps of: S202 illuminating a fundus of an eye of the subject with a light source; S204 recording, by a computer in response to an input from a trigger, input frames received from a digital video camera and an ocular lens configured for imaging a fundus of an eye of the subject; and S206 recording, by the computer in response to the input from the trigger, pulse waveform data of the subject received from a biosensor.

Step S208 of the exemplary method 200 is waiting until enough pulse waveform data has been recorded to define a low-pass frequency and a high-pass frequency, and step S210 is defining the low-pass frequency and the high-pass frequency by a lowest time and a highest time between heart beats in the pulse waveform data. Then, step S212 is stabilizing each of the input frames utilizing subpixel phase correlation with a reference frame, and step S214 is enhancing contrast of each of the input frames utilizing contrast limited adaptive histogram equalization (CLAHE).

Next, step S216 is separating each of the input frames into sub-channels, and step S218 is conducting on each sub-channel eulerian video magnification (EVM) for color amplification using the inputs of image sampling rate, the low-pass frequency, the high-pass frequency, and an amplification factor. In one embodiment, the amplification factor is a scalar. In another embodiment, the amplification factor is function-based.

Step S220 is reconstructing the amplified sub-channels into output frames, and step S222 is combining the output frames with the input frames, resulting in enhanced frames demonstrating retinal and choroidal blood flow and tissue perfusion. In one embodiment, step S224 is saving the enhanced frames sequentially to a video file. In another embodiment, step S226 is displaying the enhanced frames live on a display.

The exemplary method 200 further includes step S228 illuminating the eye of the subject with a fixation illuminator to reduce ocular movements.

Figure 4:
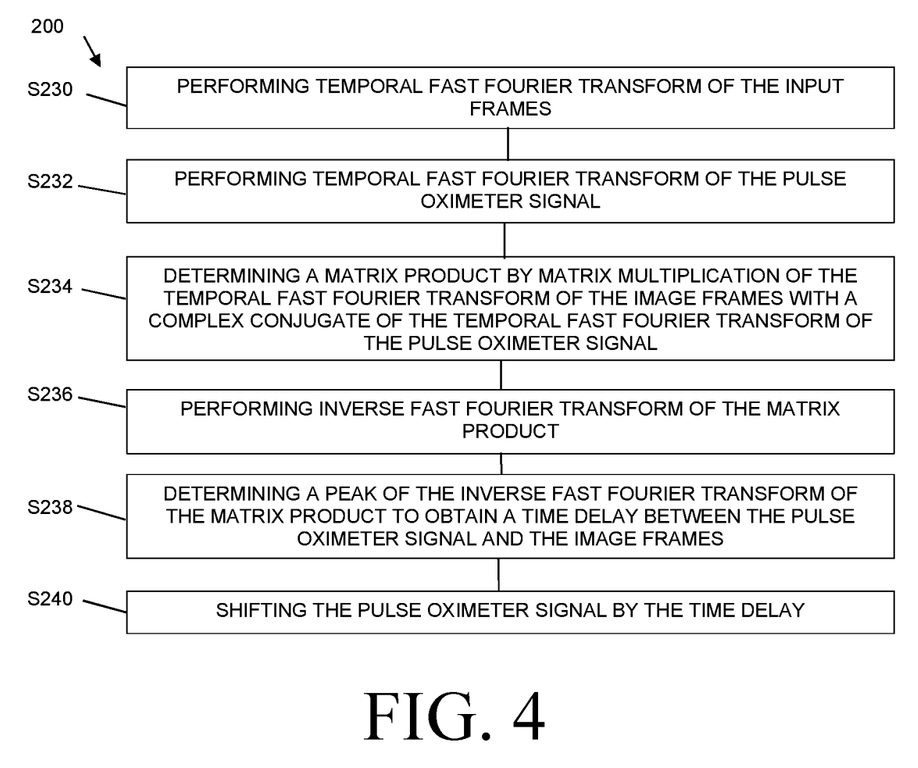
FIG. 4 is a flowchart of further steps of the exemplary method of FIG. 3.

FIG. 4 is a flowchart of further steps of the exemplary method 200 wherein the pulse waveform data is a pulse oximeter signal, which has a time delay from the perfusion in the input frames. Thus, the exemplary method 200 further comprises the steps of: S230 performing temporal fast fourier transform of the input frames; S232 performing temporal fast fourier transform of the pulse oximeter signal; S234 determining a matrix product by matrix multiplication of the temporal fast fourier transform of the image frames with a complex conjugate of the temporal fast fourier transform of the pulse oximeter signal; S236 performing inverse fast fourier transform of the matrix product; S238 determining a peak of the inverse fast fourier transform of the matrix product to obtain a time delay between the pulse oximeter signal land the image frames; and S240 shifting the pulse oximeter signal by the time delay.

Figure 5:
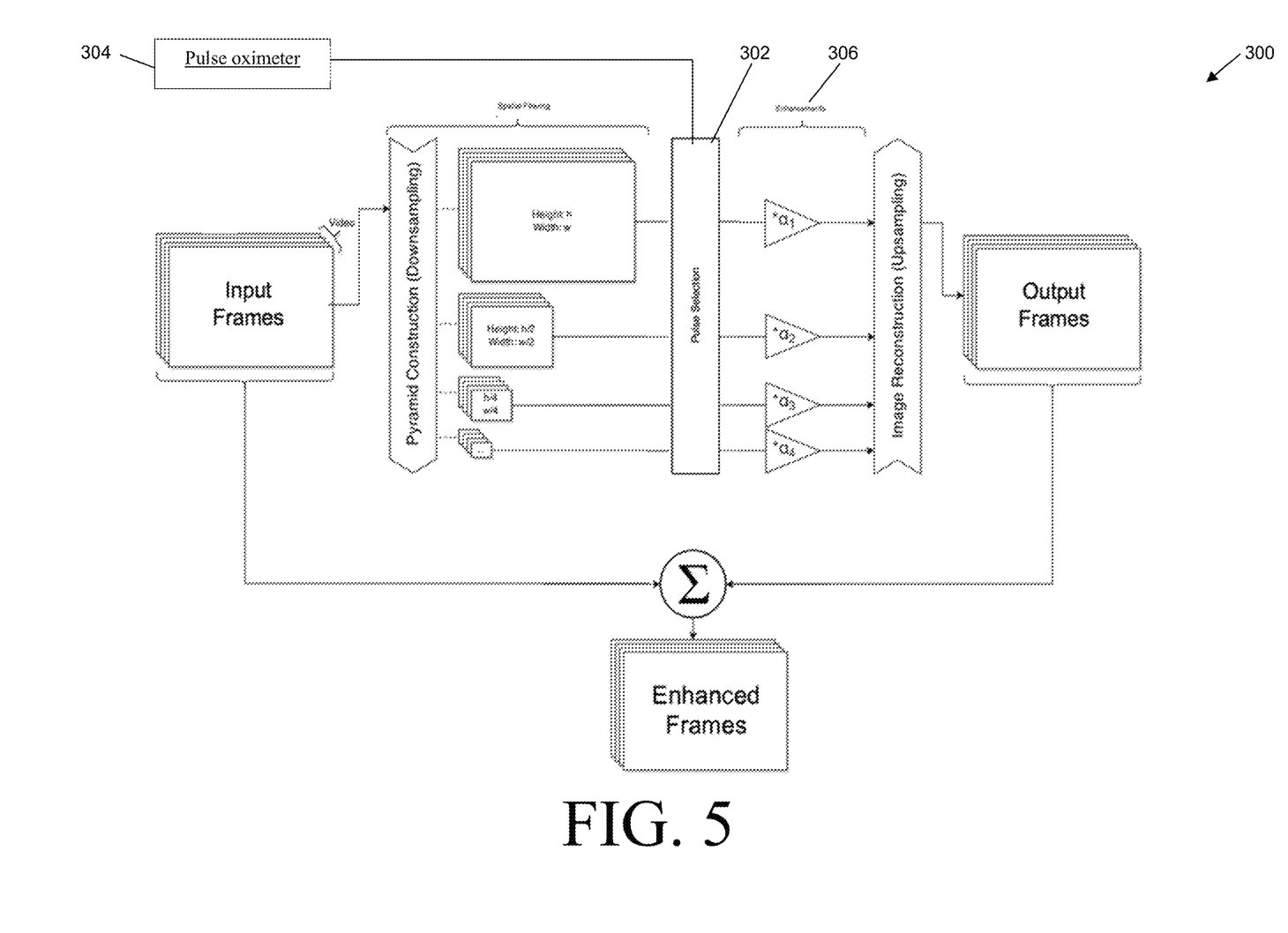
FIG. 5 is a pipeline diagram of an exemplary method according to the invention.

FIG. 5 is a pipeline diagram of an exemplary method 300 according to the invention. As shown, the EVM process includes Pyramid Construction (Downsampling), Spatial Filtering, Pulse Selection 302, Enhancements 306, and Image Reconstruction (Upsampling). However, unique to the present invention, pulse selection 302 involves input from the biosensor (pulse oximeter) 304, which cross-correlates pulse oximeter signal lag with timing of the input frames, as described above. Enhancements 306 involve amplification of temporally filtered signals with a scalar or function-based multiplication factor ($\alpha_N$) large enough to make perfusion visual without introducing signal artifacts. The image pyramids for each frame are then reconstructed and combined with the input frames, resulting in enhanced frames demonstrating tissue perfusion.

Figure 6:
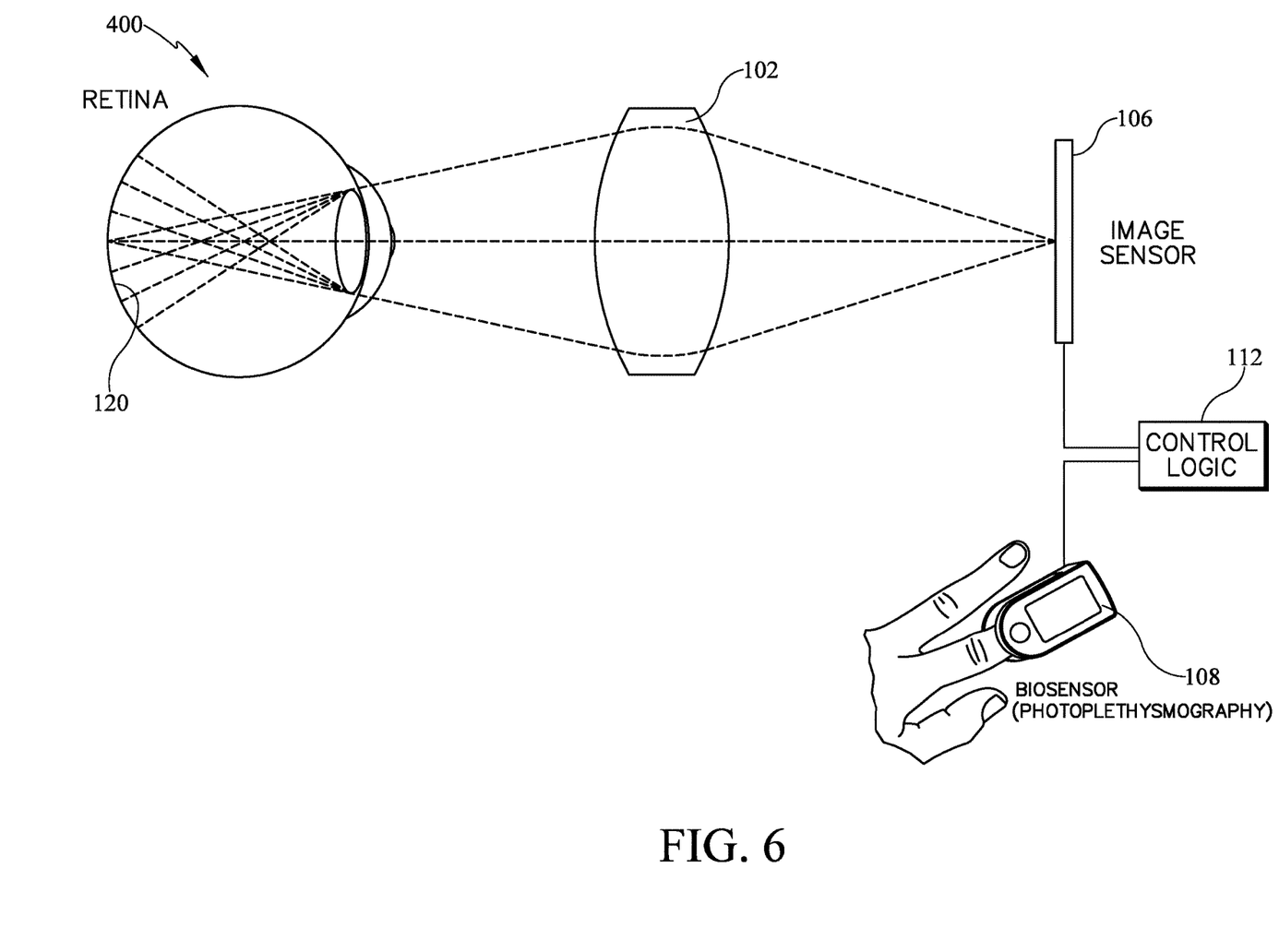
FIG. 6 is an alternate schematic diagram of an exemplary system according to the invention.

FIG. 6 is an alternate view of an exemplary system 400 according to the invention, including an ocular lens 102, a digital video camera 106, a biosensor 108, a computer 112, and a fundus of an eye 120, as described above.

Figure 7:
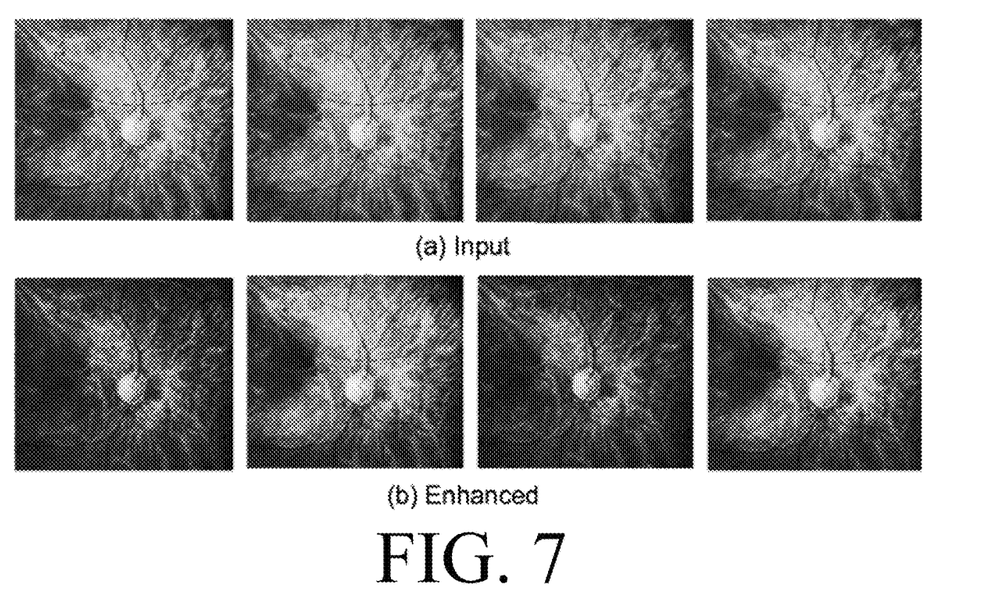
FIG. 7 includes a set of input video frames and a set of enhanced video frames following enhancement of the input video frames by the systems and methods of the invention.

FIG. 7 is a set of video frames showing four frames "(a) Input" from an original video sequence showing no change in signal intensity within the dotted area over a two-second period, and the same four frames "(b) Enhanced" following enhancement by the systems and methods described above.

Figure 8:
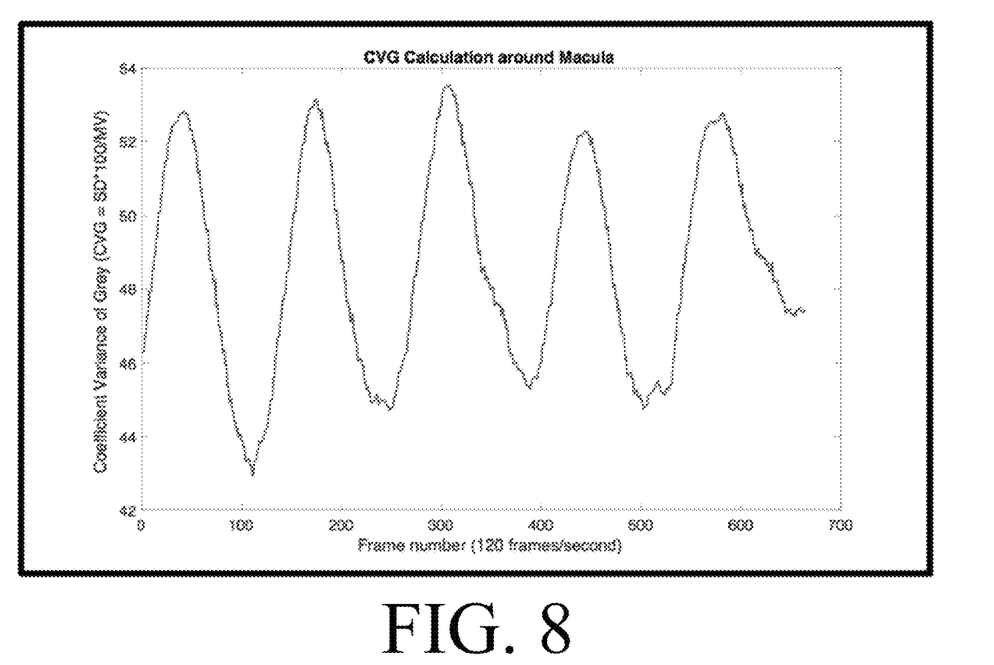
FIG. 8 is a graph of signal intensity versus time of a region of interest that has been enhanced by the systems and methods of the invention.

FIG. 8 is a graph of signal intensity versus time of a region of interest that has been enhanced by the systems and methods of the invention.

Figure 9:
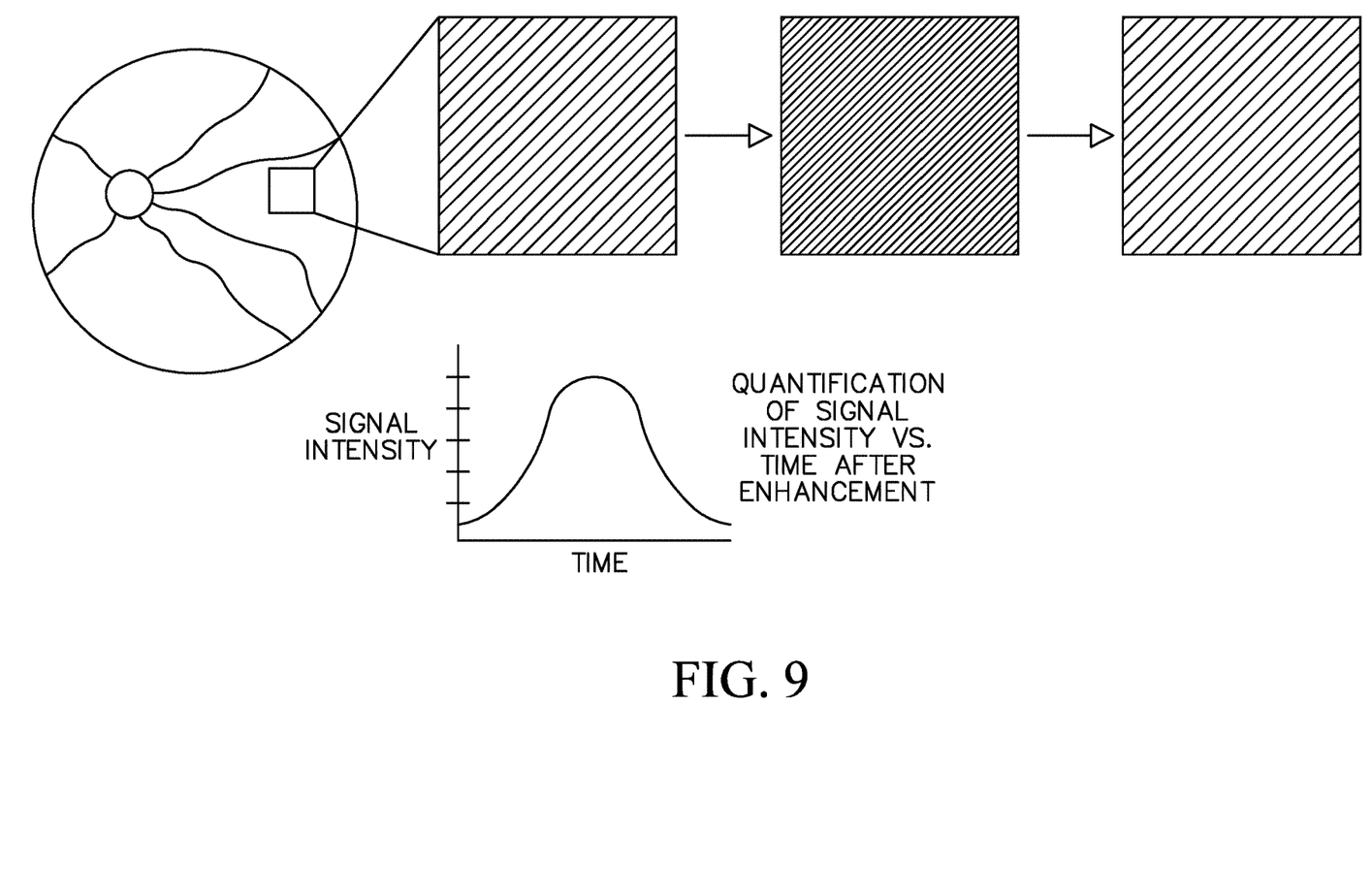
FIG. 9 is a schematic illustration of a region of interest with enhancement showing tissue perfusion over time, along with a graph illustrating quantification of signal intensity versus time after enhancement by the systems and methods of the invention.

FIG. 9 is a schematic illustration of a region of interest with enhancement showing tissue perfusion over time, along with a graph illustrating quantification of signal intensity versus time after the enhancement of the invention.

As mentioned above, the current standard, ICG angiography, requires injection of a dye that is associated with allergic reactions and takes up to an hour to complete acquiring images. Additionally, ICG injections are not recommended for certain patients with pre-existing conditions due to health complications. Advantageously, this invention can be used in areas where the equipment and dye are not available and for patients unable to undergo ICG injection. In some embodiments, invention also has capabilities of real-time image processing, advantageously creating an efficient diagnostic technique for physicians. In some embodiments, the invention allows for quantification of blood flow parameters to track how the vessels of a patient's retina are changing over multiple visits rapidly and accurately. Also, in some embodiments, the invention allows physicians to set specific regions of interest in the retina for individual patients, and track the evolution of blood flow in these designated regions over multiple patient visits. This capability truly allows the physician to better understand and study the development of diabetic retinopathy, and potentially other retinal manifestations, as it relates to choroidal-retinal blood flow.

Furthermore, in some embodiments, the invention can be used in the surgical setting, whereby surgeons can, advantageously, visualize the choroidal blood flow in real time prior to laser surgical procedures. While one embodiment of the invention focuses on color amplification for assessing blood flow, in other embodiments of the invention amplifies small motions.

In some embodiments, the processor unit specifically determines blood flow parameters for a region of interest in response to receiving a selection of the region of interest input by the operator via an input device. The processor unit, in turn, saves this region of interest for future patient visits, in order to track changes over time.

Thus, the invention performs real-time analysis, improves quality of the outputs, and allows for quantification of blood flow parameters. The region of interest magnification, in particular, allows the clinician to be more specific in the clinician's assessment of the retina of the subject and to monitor the health of the subject over an extended period of time.

Advantageously, the invention described hereinabove provides noninvasive, inexpensive, quick, and accurate visualizations of a patient's retinal blood flow to clinicians and surgeons. Additionally, the invention creates a clinical measurement for blood flow in the retina and choroid that can be tracked over time.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A system for assessing retinal and choroidal blood flow in a subject, comprising:
    an ocular lens for viewing a fundus of an eye of the subject;
    a light source for illuminating the fundus of the eye of the subject;
    a digital video camera in optical communication with the ocular lens for imaging the fundus of the eye of the subject;
    a biosensor for sensing a pulse waveform of the subject;
    a trigger;
    a computer in communication with the digital video camera, the biosensor, and the trigger, the computer configured for:
        recording input frames received from the digital video camera and pulse waveform data from the biosensor in response to an input from the trigger;
        identifying heart beats of the subject in the pulse waveform data;
        determining a shortest amount of time between the heart beats of the subject in the pulse waveform data;
        determining a longest amount of time between the heart beats of the subject in the pulse waveform data;
        defining a low-pass frequency by the shortest amount of time between the heart beats of the subject in the pulse waveform data and a high-pass frequency by the longest amount of time between the heart beats of the subject in the pulse waveform data;
        stabilizing each of the input frames utilizing subpixel phase correlation with a reference frame;
        enhancing contrast of each of the input frames utilizing contrast limited adaptive histogram equalization (CLAHE);
        separating each of the input frames into sub-channels;
        conducting on each sub-channel eulerian video magnification for color amplification using inputs of image sampling rate, the low-pass frequency, the high-pass frequency, and an amplification factor to produce amplified sub-channels;
        reconstructing the amplified sub-channels into output frames; and
        combining the output frames with the input frames, resulting in enhanced frames demonstrating retinal and choroidal blood flow and tissue perfusion; and
    a display for displaying the enhanced frames.

2. The system of claim 1, further comprising a head and chin rest for the subject to rest without strain.

3. The system of claim 1, further comprising a fixation illuminator attached to the ocular lens to reduce ocular movements.

4. The system of claim 1, wherein the biosensor is a pulse oximeter.

5. The system of claim 1, wherein the computer is further configured for adjusting the enhanced frames for brightness, contrast, zoom, or rotation.

6. The system of claim 1, wherein the computer is further configured for quantifying image intensity for a user-selected region of interest and generating a heat map of the user-selected region of interest that correlates with signal intensity changes.

7. The system of claim 1, wherein the amplification factor is a scalar.

8. The system of claim 1, wherein the amplification factor is function-based.

9. A method for assessing retinal and choroidal blood flow in a subject, comprising:
    recording, by a computer in response to an input from a trigger, input frames received from a digital video camera and an ocular lens configured for imaging a fundus of an eye of the subject;
    recording, by the computer in response to the input from the trigger, pulse waveform data of the subject received from a biosensor;
    identifying heart beats of the subject in the pulse waveform data;

determining a shortest amount of time between the heart beats of the subject in the pulse waveform data;

determining a longest amount of time between the heart beats of the subject in the pulse waveform data;

defining a low-pass frequency by the shortest amount of time between the heart beats of the subject in the pulse waveform data and a high-pass frequency by the longest amount of time between the heart beats of the subject in the pulse waveform data;

stabilizing each of the input frames utilizing subpixel phase correlation with a reference frame;

enhancing contrast of each of the input frames utilizing contrast limited adaptive histogram equalization (CLAHE);

separating each of the input frames into sub-channels;

conducting, on each sub-channel, eulerian video magnification for color amplification using inputs of image sampling rate, the low-pass frequency, the high-pass frequency, and an amplification factor to produce amplified sub-channels;

reconstructing the amplified sub-channels into output frames; and combining the output frames with the input frames, resulting in enhanced frames demonstrating tissue perfusion.

10. The method of claim 9, further comprising illuminating the eye of the subject with a fixation illuminator to reduce ocular movements.

11. The method of claim 9, further comprising saving the enhanced frames sequentially to a video file.

12. The method of claim 9, further comprising displaying the enhanced frames live on a display.

13. The method of claim 9, further comprising waiting to define the low-pass frequency and the high-pass frequency before stabilizing and enhancing the contrast of each of the input frames.

14. The method of claim 9, wherein the pulse waveform data is a pulse oximeter signal, and the method further comprising cross-correlating the pulse oximeter signal with the input frames, including:

performing temporal fast fourier transform of the input frames;

performing temporal fast fourier transform of the pulse oximeter signal;

determining a matrix product by matrix multiplication of the temporal fast fourier transform of the image frames with a complex conjugate of the temporal fast fourier transform of the pulse oximeter signal;

performing inverse fast fourier transform of the matrix product;

determining a peak of the inverse fast fourier transform of the matrix product to obtain a time delay between the pulse oximeter signal and the image frames; and shifting the pulse oximeter signal by the time delay.

15. The method of claim 9, wherein the amplification factor is a scalar.

16. The method of claim 9, wherein the amplification factor is function-based.

* * * * *